US012565555B2

(12) United States Patent
Sakamaki et al.

(10) Patent No.: US 12,565,555 B2
(45) Date of Patent: Mar. 3, 2026

(54) PHOTOCURABLE COMPOSITION, CURED PRODUCT, AND DENTAL PRODUCT

(71) Applicant: MITSUI CHEMICALS, INC., Tokyo (JP)

(72) Inventors: Toshikazu Sakamaki, Tokyo (JP); Hirohisa Shiode, Yokohama (JP); Mai Kimura, Sodegaura (JP)

(73) Assignee: MITSUI CHEMICALS, INC., Tokyo (JP)

( * ) Notice: Subject to any disclaimer, the term of this patent is extended or adjusted under 35 U.S.C. 154(b) by 1014 days.

(21) Appl. No.: 17/439,471

(22) PCT Filed: Mar. 30, 2020

(86) PCT No.: PCT/JP2020/014590

§ 371 (c)(1),
(2) Date: Sep. 15, 2021

(87) PCT Pub. No.: WO2020/203981

PCT Pub. Date: Oct. 8, 2020

(65) Prior Publication Data

US 2022/0153894 A1 May 19, 2022

(30) Foreign Application Priority Data

Mar. 29, 2019 (JP) ................................ 2019-068556

(51) Int. Cl.
*C08F 220/34* (2006.01)
*A61C 7/08* (2006.01)
*A61F 5/56* (2006.01)

(52) U.S. Cl.
CPC ............ *C08F 220/343* (2020.02); *A61C 7/08* (2013.01); *A61F 5/566* (2013.01)

(58) Field of Classification Search
CPC .. C08F 220/343; C08F 222/1065; A61C 7/08; A61F 5/566; C09D 4/00
See application file for complete search history.

(56) References Cited

U.S. PATENT DOCUMENTS

| | | | | |
|---|---|---|---|---|
| 6,017,973 | A | 1/2000 | Tamura et al. | |
| 6,136,881 | A | 10/2000 | Sekiguchi et al. | |
| 6,353,039 | B1 * | 3/2002 | Rheinberger .......... | A61K 6/836 524/404 |
| 2011/0288195 | A1 * | 11/2011 | Kajikawa ................. | A61K 6/30 522/11 |
| 2012/0296061 | A1 | 11/2012 | Naruse et al. | |
| 2017/0360534 | A1 | 12/2017 | Sun et al. | |
| 2018/0282455 | A1 | 10/2018 | Sakamaki et al. | |
| 2022/0153894 | A1 | 5/2022 | Sakamaki et al. | |

FOREIGN PATENT DOCUMENTS

| | | | |
|---|---|---|---|
| CN | 109517105 | A | 3/2019 |
| JP | H08311115 | A | 11/1996 |
| JP | H1179925 | A | 3/1999 |
| JP | 2006028499 | A | 2/2006 |
| JP | 2019-199448 | A | 11/2019 |
| JP | 2022-159302 | A | 10/2022 |
| JP | 7662512 | B2 | 4/2025 |
| KR | 10-1957204 | B1 | 3/2019 |
| WO | 2012157568 | A1 | 11/2012 |
| WO | 2017/006173 | A1 | 1/2017 |
| WO | 2017/061446 | A1 | 4/2017 |
| WO | 2017223084 | A1 | 12/2017 |
| WO | 2018038056 | A1 | 3/2018 |
| WO | 2018105463 | A1 | 6/2018 |

* cited by examiner

*Primary Examiner* — Jessica M Roswell

(74) *Attorney, Agent, or Firm* — BUCHANAN INGERSOLL & ROONEY PC

(57) ABSTRACT

A photo-curable composition including a di-(meth)acrylic monomer (A) having two (meth)acryloyloxy groups and two urethane bonds, an acrylic monomer (B) having one acryloyl group, and a photopolymerization initiator, as well as a cured product of the photo-curable composition, and a dental product including the cured product.

16 Claims, 1 Drawing Sheet

PHOTOCURABLE COMPOSITION, CURED PRODUCT, AND DENTAL PRODUCT

TECHNICAL FIELD

The present invention relates to a photo-curable composition, a cured product, and a dental product.

BACKGROUND ART

Today, resins are used for various applications, and characteristics corresponding to each application are required. For example, dental mouthpieces are used for the treatment of temporomandibular disorder or the orthodontic therapy.

Currently, for producing a dental mouthpiece, a method, in which a resin sheet, or the like is softened by heating with hot water or otherwise, and then pressed against a model to be molded, followed by photopolymerization, or heat polymerization, is widely applied.

An acrylic resin is mainly used as the resin material for the dental mouthpiece, and for example, a photo-curable composition for a splint including a urethane dimethacrylate such as di-2-methyloxyethyl-2,2,4-trimethylhexamethylene dicarbamate (UDMA), a bifunctional methacrylate having no urethane bond such as 1,3-butylene glycol dimethacrylate, a urethane oligomer, and an inorganic filler such as silica has been disclosed in the Example of Japanese Patent Application Laid-Open (JP-A) No. H11-79925.

SUMMARY OF INVENTION

Technical Problem

Of the dental mouthpieces, a splint used for treating temporomandibular disorder, a mouthpiece used for orthodontic therapy or for preventing bruxism, or a retainer for maintaining the corrected dentition, is used for correcting or maintaining the dentition, so some hardness and strength are required. At the same time, since it is used for the extended time period in the oral cavity, too high hardness fosters a feeling of discomfort when the same is attached. Therefore, it is desirable that the flexural strength and flexural modulus should not be too high. However, when the flexural strength and flexural modulus are lowered, it becomes difficult to maintain the strength (i.e. toughness), and therefore the hardness can be hardly controlled within an appropriate range while maintaining the strength.

As described above, the dental mouthpiece is required to have a certain degree of hardness, but in a case in which the hardness is too high, it may cause a pain or an uncomfortable feeling when used in the oral cavity. This is a serious problem in the field of dentistry. On the other hand, when the hardness is suppressed, it is difficult to keep the toughness high, and unless the toughness is high enough, it cannot withstand long-term use. That is, it is desirable that the toughness is high while keeping the hardness in an appropriate range, and a resin material having both a high strength and a reasonable range of hardness has been demanded.

An object of this disclosure is to provide a photo-curable composition capable of exhibiting, when photo-cured, a high value of total work of fracture, which is an index of toughness, while keeping the flexural strength and flexural modulus, which are indexes of hardness, in an appropriate range. Another object is to provide a cured product of the photo-curable composition, and a dental product including the cured product.

Solution to Problem

As a result of diligent studies, the present inventors have found that a photo-curable composition including a di(meth) acrylic monomer (A) having two (meth)acryloyloxy groups and two urethane bonds, an acrylic monomer (B) having one acryloyl group, and a photopolymerization initiator exhibits superior toughness, and a reasonable range flexural strength and flexural modulus after photo-curing, thereby completing the present invention.

That is, the specific means for achieving the above objects are as follows.

<1> A photo-curable composition including a di-(meth) acrylic monomer (A) having two (meth)acryloyloxy groups and two urethane bonds, an acrylic monomer (B) having one acryloyl group, and a photopolymerization initiator.

<2> The photo-curable composition according to <1>, wherein the ratio of the number of acryloyl groups to the total number of acryloyl groups and methacryloyl groups in the photo-curable composition is 10% or more.

<3> The photo-curable composition according to <1> or <2>, wherein a cured product obtained by curing a photo-curable composition exhibits a flexural strength of from 50 to 70 MPa, a flexural modulus of from 1,500 to 2,000 MPa, and a total work of fracture of 250 $J/m^2$ or more.

<4> The photo-curable composition according to any one of <1> to <3>, wherein the di-(meth)acrylic monomer (A) is a compound represented by the following Formula (1):

(1)

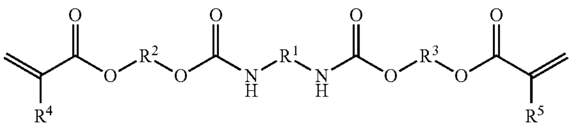

(In Formula (1), $R^1$ is a divalent chain hydrocarbon group, a divalent hydrocarbon group having an aromatic structure, or a divalent hydrocarbon group having an alicyclic structure, each of $R^2$ and $R^3$ is independently a divalent chain hydrocarbon group having optionally a substituent, and each of $R^4$ and $R^5$ is independently a methyl group or a hydrogen atom.)

<5> The photo-curable composition according to <4>, wherein in Formula (1), $R^1$ is a C6-C12 divalent hydrocarbon group having an aromatic structure, or a C6-C12 divalent hydrocarbon group having an alicyclic structure, and each of $R^2$ and $R^3$ is independently a C6-C12 divalent chain hydrocarbon group having no substituent.

<6> The photo-curable composition according to any one of <1> to <5>, wherein the acrylic monomer (B) includes at least one of a compound represented by the following Formula (2) and a compound represented by the following Formula (3):

(2)

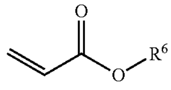

-continued (3)

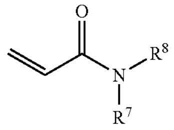

(In Formula (2), $R^6$ is a monovalent organic group which may have a ring structure. In Formula (3), each of IC and $R^8$ is independently a monovalent organic group which may have a ring structure, or a hydrogen atom, and $R^7$ and $R^8$ may together form a ring.)

<7> The photo-curable composition according to <6>, wherein the acrylic monomer (B) includes a compound represented by Formula (2), and $R^6$ in Formula (2) is a C6-C20 monovalent organic group having a ring structure.

<8> The photo-curable composition according to any one of <1> to <7>, wherein the weight average molecular weight of the di-(meth)acrylic monomer (A) is from 380 to 700.

<9> The photo-curable composition according to any one of <1> to <8>, wherein the weight average molecular weight of the acrylic monomer (B) is from 130 to 320.

<10> The photo-curable composition according to any one of <1> to <9>, wherein the content of the di-(meth) acrylic monomer (A) is from 300 parts by mass to 950 parts by mass with respect to 1000 parts by mass of the total content of (meth)acrylic monomer components contained in the photo-curable composition.

<11> The photo-curable composition according to any one of <1> to <10>, wherein the total content of the di-(meth)acrylic monomer (A) and the acrylic monomer (B) is 800 parts by mass or more with respect to 1000 parts by mass of the total content of (meth)acrylic monomer components contained in the photo-curable composition.

<12> A photo-curable composition including a photopolymerizable component and a photopolymerization initiator, wherein a cured product obtained by curing a photo-curable composition exhibits a flexural modulus from 1500 MPa to 2500 MPa, and a total work of fracture of 250 $J/m^2$ or more.

<13> The photo-curable composition according to any one of <1> to <12>, wherein the viscosity measured using an E type viscometer at 25° C. and 50 rpm is from 20 mPa·s to 3000 mPa·s.

<14> The photo-curable composition according to any one of <1> to <13> for optical shaping.

<15> A cured product of the photo-curable composition according to any one of <1> to <14>.

<16> A dental product including the cured product of the photo-curable composition according to <15>.

<17> The dental product according to <16>, wherein the dental product is a medical device which is used in an oral cavity.

Advantageous Effects of Invention

According to this disclosure, a photo-curable composition which is superior in fracture toughness and has a flexural strength and a flexural modulus in reasonable ranges after photo-curing can be provided.

Further, according to an aspect of the present invention a cured product of the photo-curable composition and a dental product including the cured product of the photo-curable composition are provided.

DESCRIPTION OF EMBODIMENTS

Figure 1A:
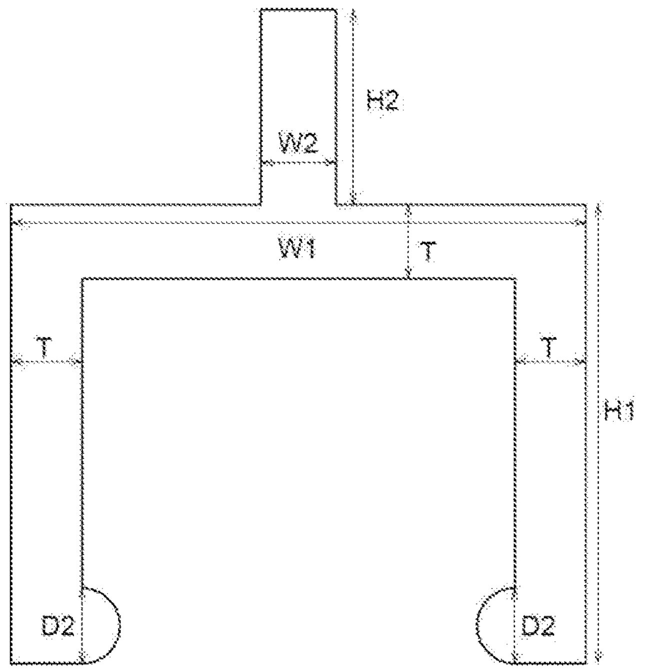
FIG. 1A shows the shape of an attachment and detachment test piece for an attachment and detachment test

Herein, a numerical range expressed by "x to y" includes the values of x and y in the range as the minimum and maximum values, respectively.

Further, "(meth)acrylic monomer" is herein a concept that includes both an acrylic monomer and a methacrylic monomer.

Further, "(meth)acryloyloxy group" is herein a concept that includes both an acryloyloxy group and a methacryloyloxy group. The description of "acryloyloxy group" or "methacryloyloxy group" means only the designated group.

"Urethane bond" herein refers to —NHC(=O)O— bond.

[Photo-Curable Composition]

The photo-curable composition according to this disclosure is a photo-curable composition that contains a photopolymerizable component, and a photopolymerization initiator.

The photopolymerizable component preferably includes a di-(meth)acrylic monomer (A) having two (meth)acryloyloxy groups and two urethane bonds, and an acrylic monomer (B) having one acryloyl group.

When the photo-curable composition of this disclosure includes a di-(meth)acrylic monomer (A) having two (meth) acryloyloxy groups and two urethane bonds, an acrylic monomer (B) having one acryloyl group, and a photopolymerization initiator, it can exhibit a superior fracture toughness and a flexural strength and a flexural modulus in reasonable ranges after photo-curing.

Therefore, an optically shaped product produced by optical shaping using a photo-curable composition of this disclosure and a dental product including the optically shaped product can also exhibit a superior fracture toughness and a flexural strength and a flexural modulus in reasonable ranges as well as ease of attachment and detachment and a favorable durability when the attachment and detachment are repeated.

The "ratio of the number of acryloyl groups to the total number of acryloyl groups and methacryloyl groups in the photo-curable composition" herein is a value expressed in % obtained by dividing the number of all the acryloyl groups by the total number of all the acryloyl groups and methacryloyl groups contained in the photo-curable composition, and multiplying the quotient by 100.

With respect to the photo-curable composition of this disclosure, the ratio of the number of acryloyl groups to the total number of acryloyl groups and methacryloyl groups in the photo-curable composition is preferably 10% or more. When it is 10% or more, the toughness can be enhanced. From the viewpoint of enhancement of toughness, the ratio of the number of acryloyl groups to the total number of acryloyl groups and methacryloyl groups in the photo-curable composition is more preferably 20% or more, still more preferably 30% or more, still more preferably 40% or more, still more preferably 50% or more, 60% or more, or 70% or more, and particularly preferably 100%.

A photo-cured product obtained by photo-curing a photo-curable composition of this disclosure preferably has a flexural strength in a range of 50 MPa to 100 MPa, a flexural modulus in a range of 1500 MPa to 2500 MPa, and a total work of fracture of 250 $J/m^2$ or more. When the flexural strength, flexural modulus, and total work of fracture respectively satisfy the aforedescribed ranges, the obtained photo-cured product is superior in toughness, and has a hardness in a reasonable range.

When the flexural strength is 50 MPa or more, and the flexural modulus is 1500 MPa or more, for example, the hardness of a dental product using a cured product of a photo-curable composition of this disclosure can be practically sufficient. When the flexural strength is 100 MPa or less, and the flexural modulus is 2500 MPa or less, and a cured product of such a photo-curable composition of this disclosure is used, for example, in a medical device to be used in the oral cavity, a comfortable feel of use can be obtained without causing pain.

In a cured product obtained by curing a photo-curable composition of this disclosure, the flexural modulus is more preferably from 1500 to 2500 MPa, and particularly preferably 2000 MPa or less. A suitable range of the flexural modulus is, for example, from 1500 MPa to 2500 MPa, or from 1500 MPa to 2000 MPa. Further, the total work of fracture is preferably 250 $J/m^2$ or more. Within these ranges, a better feel of use and strength can be obtained. The total work of fracture is more preferably 300 $J/m^2$ or more, still more preferably 400 $J/m^2$ or more, and particularly preferably 500 $J/m^2$ or more. Although the upper limit of the total work of fracture does not need to be specified, it is preferably, for example, less than 1100 $J/m^2$.

By satisfying the aforedescribed ranges, when a medical device such as a splint to be used in the oral cavity is constructed therewith, a comfortable feel of use is obtained without causing pain, and removal of the attached device can be easy Further, when the flexural modulus is 2500 MPa or less, and also the total work of fracture is 250 $J/m^2$ or more, and this cured product is used in a medical device to be used in the oral cavity, attachment and detachment of the device is easy and durability in repeating the attachment and detachment can be excellent As described in ISO 20795-2, by setting the flexural strength at 50 MPa or more, and the flexural modulus at 1500 MPa or more, and when a cured product of a photo-curable composition of this disclosure is used in a medical device to be used in the oral cavity, a favorable feel of use, strength, and durability can be obtained.

A photo-cured product obtained by photo-curing a photo-curable composition of this disclosure more preferably has a flexural strength in a range from 50 MPa to 70 MPa, a flexural modulus in a range from 1500 MPa to 2000 MPa, and a total work of fracture of 250 $J/m^2$ or more. The total work of fracture is still more preferably 300 $J/m^2$ or more, still more preferably 400 $J/m^2$ or more, and particularly preferably 500 $J/m^2$ or more. By setting the flexural modulus in the above range, and when a cured product of a photo-curable composition of this disclosure is used, for example, in a medical device to be used in the oral cavity, a pain is less likely to develop and a better feel of use can be obtained. When the flexural modulus is suppressed, while the total work of fracture is kept high, the medical device gives a favorable feel of use, and can exhibit superior strength. Further, by setting the flexural modulus and the total work of fracture in the above ranges, and when the cured product is used in a medical device to be used in the oral cavity, attachment and detachment of the medical device is easy and its durability in repeating the attachment and detachment can be excellent For measuring a flexural strength and a flexural modulus, a photo-curable composition of this disclosure is shaped into a shaped product in a size of 64 mm×10 mm×thickness 3.3 mm, which is then photo-cured by irradiation with ultraviolet rays under the condition of 10 $J/cm^2$ into an optically shaped product (that is, cured product; the same applies also hereinafter), the obtained optically shaped product is stored in a thermostatic water bath at 37±1° C. for 50±2 hours, and after the storage the flexural strength and the flexural modulus are measured according to ISO 20795-1:2008 (or JIS T 6501: 2012).

Meanwhile, the total work of fracture ($J/cm^2$) is determined by a fracture toughness test by a bending test. A photo-curable composition of this disclosure is shaped into a shaped product in a size of 39 mm×8 mm×thickness 4 mm, which is then photo-cured by irradiation with ultraviolet rays under the condition of 10 $J/cm^2$ into an optically shaped product, the obtained optically shaped product is notched according to ISO 20795-1:2008, then stored in a thermostatic water bath at 37±1° C. for 7 days±2 hours, and after the storage a fracture toughness test by a bending test is performed under the condition of push-in speed of 1.0±0.2 mm/min to measure the total work of fracture ($J/m^2$).

The photo-curable composition of this disclosure may be used suitably for optical shaping. The "optical shaping" means herein a kind of three-dimensional modeling methods using a 3D printer.

Examples of an optical shaping method include an SLA (Stereo Lithography Apparatus) method, a DLP (Digital Light Processing) method, and an ink jet method.

The photo-curable composition of the present Embodiment is particularly suitable for the SLA method and the DLP method.

Examples of the SLA method include a method by which a three-dimensional shaped product is obtained by irradiating a photo-curable composition with spot-shaped ultraviolet laser light.

For producing a dental product or the like by the SLA method, for example, a photo-curable composition of this Embodiment is retained in a vat, the liquid surface of the photo-curable composition is selectively irradiated with spot-shaped ultraviolet laser light so that a desired pattern is drawn to cure the photo-curable composition, thereby creating a cured layer with a desired thickness on the shaping table. Then the shaping table is lowered to supply a liquid photo-curable composition in an amount necessary for another layer on the cured layer, which is then cured similarly. The above layering procedure is repeated for making consecutive cured layers. By doing so, a dental product etc. can be produced.

Examples of the DLP method include a method of producing a three-dimensional shaped product by irradiating a photo-curable composition with planar light.

With respect to the method of producing a three-dimensional shaped product by the DLP method, the description of Japanese Patent No. 5111880 or Japanese Patent No. 5235056 can be referred to as appropriate.

When a dental product or the like is produced by the DLP method, for example, a lamp, or an LED, which emits light other than laser light, such as a high-pressure mercury lamp, an ultra-high pressure mercury lamp, or a low-pressure mercury lamp, is used as a light source, a planar drawing mask in which a plurality of digital micromirror shutters are arranged in a planar manner is placed between the light source and the shaping surface of the photo-curable composition, and the shaping surface of the photo-curable composition is irradiated with light through the planar drawing mask so as to layer a cured layer of a predetermined pattern one on another. By doing so, a dental product etc. can be produced.

Examples of the inkjet method include a method of producing a three-dimensional shaped product in which droplets of a photo-curable composition are consecutively extruded through an ink jet nozzle onto a substrate, and the droplets stuck to the substrate are irradiated with light.

When a dental product or the like is produced by the inkjet method, for example, a photo-curable composition is extruded through an ink jet nozzle to a substrate by scanning a head equipped with an ink jet nozzle and a light source in a plane, and the extruded photo-curable composition is irradiated with light to form a cured layer. The above operation is repeated to layer a cured layer one on another. By doing so, a dental product etc. can be produced.

The viscosity measured by an E type viscometer at 25° C. and 50 rpm of the photo-curable composition of this disclosure is preferably from 20 mPa·s to 5000 mPa·s from the viewpoint of suitability for production of a dental product by optical shaping. The lower limit of the viscosity is more preferably 50 mPa·s. The upper limit of the viscosity is more preferably 3000 mPa·s, still more preferably 2000 mPa·s, still more preferably 1500 mPa·s, and particularly preferably 1200 mPa·s.

Next, the components of the photo-curable composition of this disclosure will be described.

The photo-curable composition of this disclosure contains at least one photopolymerizable component.

Examples of the photopolymerizable composition include a compound having an ethylenic double bond.

Examples of the compound having an ethylenic double bond include a (meth)acrylic monomer, styrene, a styrene derivative, and (meth)acrylonitrile.

As the photopolymerizable component, a photopolymerizable component described in the paragraph 0030 to paragraph 0059 of International Publication No. WO 2019/189652 may be used.

The photopolymerizable component should preferably contain at least one (meth)acrylic monomer.

There is no additional restriction on a (meth)acrylic monomer composing the (meth)acrylic monomer component, insofar as it is a monomer having one or more (meth)acryloyl groups in the molecule.

The (meth)acrylic monomer may be a monofunctional (meth)acrylic monomer (i.e., a monomer having one (meth) acryloyl group in the molecule), a bifunctional (meth)acrylic monomer (i.e., a monomer having two (meth)acryloyl groups in the molecule), or a multifunctional (meth)acrylic monomer (i.e., a trifunctional or higher (meth)acrylic monomer; that is a monomer having three or more (meth)acryloyl groups in the molecule).

The photopolymerizable component in the photo-curable composition of this disclosure preferably includes at least either of di-(meth)acrylic monomer (A) having two (meth) acryloyloxy groups and two urethane bonds, and an acrylic monomer (B) having one acryloyl group, and more preferably includes both the di-(meth)acrylic monomer (A) and the acrylic monomer (B).

When the photopolymerizable component includes at least either (preferably both) of the di-(meth)acrylic monomer (A) and the acrylic monomer (B), the aforedescribed preferable ranges of the flexural modulus and/or the total work of fracture can be easily met.

As a method for regulating the flexural modulus and flexural strength while maintaining the total work of fracture, there is a method in which the kind and ratio of the acrylic monomer (B) are adjusted. For example, by increasing the aromatic ring concentration of the acrylic monomer (B), the flexural modulus and flexural strength can be increased while maintaining the total work of fracture, and by decreasing the aromatic ring concentration, the flexural modulus and flexural strength can be reduced while maintaining the total work of fracture. Further, by increasing the aromatic ring concentration of the acrylic monomer (A) the total work of fracture can be improved. In particular, by increasing the content of the acrylic monomer (B), it becomes easier to achieve improvement of the total work of fracture and regulate the flexural modulus and the flexural strength to a low level.

<Di-(meth)acrylic Monomer (A) Having Two (meth)acryloyloxy Groups and Two Urethane Bonds>

The photo-curable composition of this disclosure preferably includes a di-(meth)acrylic monomer (A) having two (meth)acryloyloxy groups and two urethane bonds. The di-(meth)acrylic monomer (A) has no (meth)acryloyloxy group other than the two (meth)acryloyloxy groups. The di-(meth)acrylic monomer (A) has no urethane bond other than the two urethane bonds.

As the di-(meth)acrylic monomer (A), one kind, or two or more kinds of di-(meth)acrylic monomers may be used, insofar as they are di-(meth)acrylic monomers having two (meth)acryloyloxy groups and two urethane bonds.

The di-(meth)acrylic monomer (A) is preferably a compound represented by the following Formula (1).

(1)

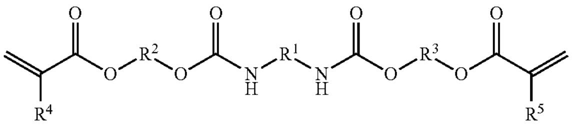

In Formula (1), $R^1$ is a divalent chain hydrocarbon group, a divalent hydrocarbon group having an aromatic structure, or a divalent hydrocarbon group having an alicyclic structure; each of $R^2$ and $R^3$ is independently a divalent chain hydrocarbon group which may have a substituent; and each of $R^4$ and $R^5$ is independently a methyl group, or a hydrogen atom.

In Formula (1), $R^1$ is preferably a divalent hydrocarbon group having an aromatic structure, or a divalent hydrocarbon group having an alicyclic structure. When $R^1$ includes a ring structure, the viscosity is suppressed, the toughness is improved, and the flexural strength and flexural modulus fall within appropriate ranges.

In Formula (1), the carbon number of the divalent chain hydrocarbon group of $R^1$ is preferably from 1 to 20, more preferably from 1 to 10, and particularly preferably from 2 to 6. The divalent chain hydrocarbon group may be in a form of normal chain or branched chain, may be saturated or unsaturated, and may have a substituent. It is preferably a normal chain or branched chain alkylene group having a carbon number from 1 to 20, more preferably a normal chain or branched chain alkylene group having a carbon number from 1 to 12, and particularly preferably a normal chain or branched chain alkylene group having a carbon number from 1 to 10.

Specific examples of the normal chain or branched chain C1-C20 divalent alkylene group include a methylene group, an ethylene group, a propanediyl group, a butanediyl group, a pentanediyl group, a hexanediyl group, a heptanediyl group, a octanediyl group, a nonanediyl group, a decanediyl group, an undecanediyl group, a dodecanediyl group, a tridecanediyl group, a tetradecanediyl group, a pentadecanediyl group, an octadecanediyl group, an eicosylene group, a vinylene group, a propenediyl group, a butenediyl group, a pentenediyl group, an ethynylene group, propynylene, and a 2,4,4-trimethylhexylene group, which may be in a normal chain or branched chain form. Among these, a 2,4,4-trimethylhexylene group is particularly preferable.

The divalent hydrocarbon group having an aromatic structure of $R^1$ in Formula (1) is preferably a divalent hydrocarbon group having an aromatic structure which may have a substituent, and a carbon number from 6 to 20. The carbon number is more preferably from 6 to 12, and particularly preferably from 6 to 10.

Examples of the divalent hydrocarbon group having an aromatic structure include an arylene group, an alkylene arylene group, an alkylene arylene alkylene group, and an arylene alkylene arylene group.

$R^1$ is preferably an alkylene arylene group, or an alkylene, because the viscosity can be suppressed, and a high total work of fracture can be obtained, while keeping the flexural strength and the flexural modulus at reasonable levels.

Specific examples of an arylene group, an alkylene arylene group, an alkylene arylene alkylene group, an alkylarylene group, and an arylene alkylene arylene group include 1,3- or 1,4-phenylene group, 1,3- or 1,4-phenylenedimethylene group, and 1,3- or 1,4-phenylenediethylene group.

The divalent hydrocarbon group having an alicyclic structure of $R^1$ in Formula (1) preferably has a carbon number from 3 to 20, more preferably from 6 to 12, and particularly preferably from 6 to 8.

Examples of the alicyclic structure include a cyclopropylene group, a cyclobutylene group, a cyclopentylene group, a cyclohexylene group, a cyclohexenylene group, a cycloheptylene group, a cyclooctylene group, a cyclononylene group, a cyclodecylene group, a cycloundecylene group, a cyclododecylene group, a cyclotridecylene group, a cyclotetradecylene group, a cyclopentadecylene group, a cyclooctadecylene group, a cycloicosilene group, a bicyclohexylene group, a norbornylene group, an isobornylene group, and an adamantylene group. Among these, a norbornylene group, and an isobornylene group are preferable.

When $R^1$ is a divalent hydrocarbon group having an alicyclic structure, a particularly suitable example is as follows. "*" represents the bond position.

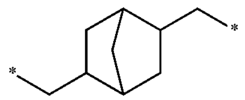
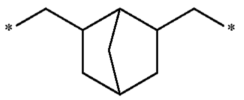
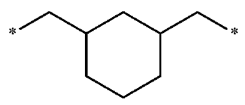
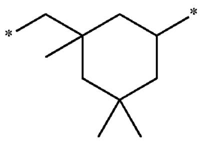

-continued

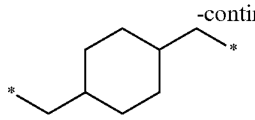

$R^1$ in Formula (1) may have a substituent, and examples of the substituent include a normal chain or branched chain C1-C6 alkyl group.

The divalent hydrocarbon group having an alicyclic structure of $R^1$ in Formula (1) is preferably a divalent hydrocarbon group having a structure in which two divalent alkylene groups which may be the same or different (for example, C1-C3 alkylene groups) are bonded to an alicyclic structure via each one of the respective vacant bonds (that is, the structure in which an alicyclic structure is bonded between the two divalent alkylene groups), or a divalent hydrocarbon group having a structure in which one divalent alkylene group (for example, a C1-C3 alkylene group) is bonded to an alicyclic structure via one of the vacant bonds, and more preferably the one in which an alicyclic structure is between two methylene groups, or the one in which one methylene group is bonded with an alicyclic structure via one of the vacant bonds.

In Formula (1), each of $R^1$ and $R^3$ is independently a divalent chain hydrocarbon group which may have a substituent. The divalent chain hydrocarbon groups suitable for $R^1$ and $R^3$ are the same as the divalent chain hydrocarbon groups suitable for $R^1$. However, $R^1$ and $R^3$ more preferably have a carbon number from 2 to 6, and more preferably a carbon number from 2 to 3. Further, from the viewpoint of suppression of the viscosity, a not substituted divalent chain hydrocarbon group having a carbon number from 2 to 6 is more preferable, and that having a carbon number from 2 to 3 is particularly preferable.

When $R^1$ or $R^3$ has a substituent, examples of the substituent include a C1-C6 alkyl group, such as a methyl group, and an ethyl group; an aryl group; a C3-C6 cycloalkyl group, such as a cyclopentyl group, and a cyclohexyl group; a tolyl group; a xylyl group; a cumyl group; a styryl group; and an alkoxyphenyl group, such as a methoxyphenyl group, an ethoxyphenyl group, and a propoxyphenyl group.

Examples of a suitable compound for the di-(meth)acrylic monomer (A) include a urethane diacrylic monomer which is a reaction product between an isocyanate selected from the group consisting of m-xylylene diisocyanate, tetramethylxylylene diisocyanate, norbornene diisocyanate, and isophorone diisocyanate, and a hydroxy acrylate selected from the group consisting of hydroxyethyl acrylate, hydroxypropyl acrylate, and 4-hydroxybutyl acrylate; and the di-(meth) acrylic monomers (A) used in Examples described later.

The weight average molecular weight of the di-(meth) acrylic monomer (A) is preferably from 380 to 700, and more preferably from 400 to 650.

The di-(meth)acrylic monomer (A) may be synthesized from a commercially available monomer. For example, a di-(meth)acrylic monomer (A) may be synthesized from two molecules of a hydroxy (meth)acrylate and one molecule of a diisocyanate.

Examples of a suitable hydroxy (meth)acrylate include the following. In the following structures, "Et" represents an ethyl group.

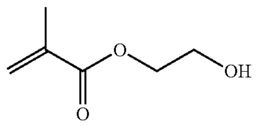
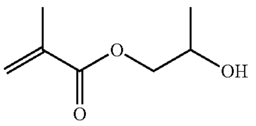

-continued

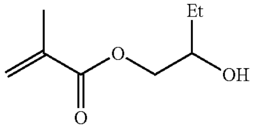

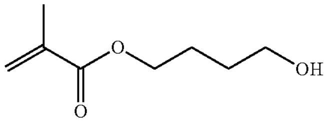

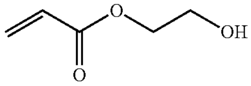

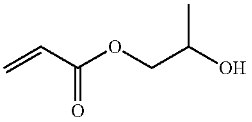

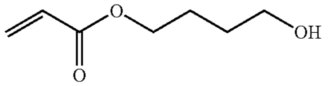

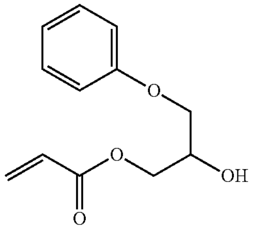

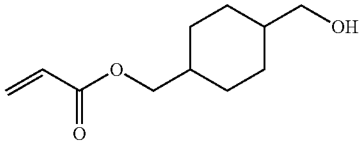

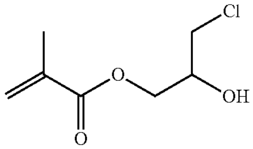

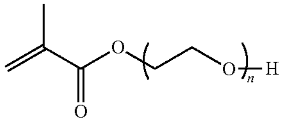

n ≈ 2, 4.5

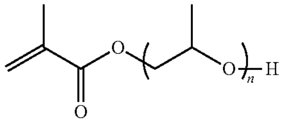

n ≈ 4 ~ 6

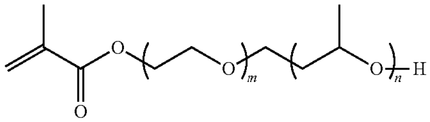

m ≈ 3.5 n ≈ 2.5

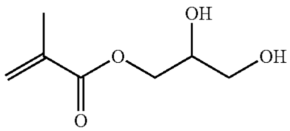

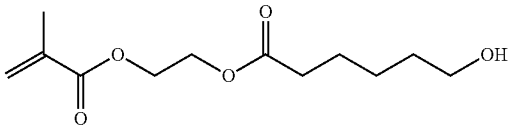

-continued

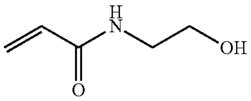

Examples of a suitable diisocyanate include the following. In the following structures, "Me" represents a methyl group.

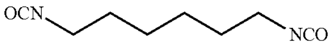

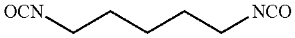

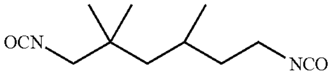

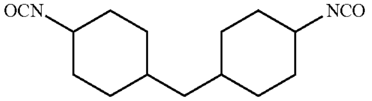

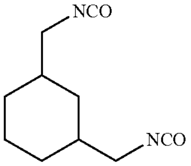

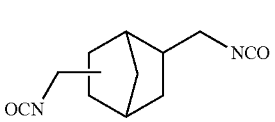

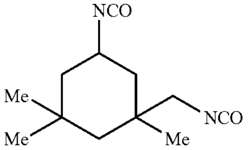

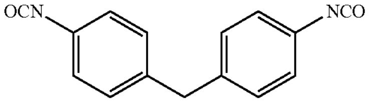

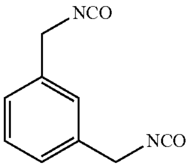

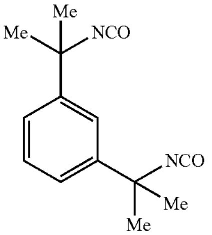

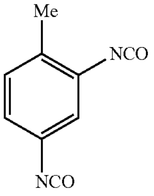

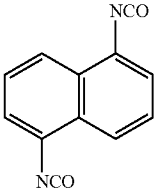

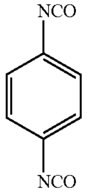

<Acrylic Monomer (B) Having One Acryloyl Group>

The photo-curable composition of this disclosure includes an acrylic monomer (B) having one acryloyl group. The acrylic monomer (B) has no acryloyl group other than the one acryloyl group.

As the acrylic monomer (B), only one kind, or two or more kinds may be used, insofar as they are acrylic monomers having one acryloyl group.

The acrylic monomer (B) is preferably a compound represented by the following Formula (2) or (3).

(2)

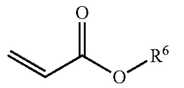

(3)

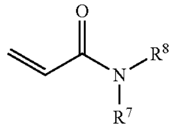

$R^6$ in Formula (2) is a monovalent organic group which may have a ring structure.

Each of $R^7$ and $R^8$ in Formula (3) is independently a monovalent organic group which may have a ring structure, or a hydrogen atom, and $R^7$ and $R^8$ may bond together to form a ring.

The acrylic monomer (B) is preferably a compound represented by Formula (2), and $R^6$ is preferably a C3-C30 monovalent organic group which has a ring structure, and more preferably a C6-C20 monovalent organic group which has a ring structure.

In Formula (2), $R^6$ may have a structure represented by the following Formula (4).

$*-L_1-A$ (4)

In Formula (4), the $L_1$ is a single bond or a C1-C30 divalent chain hydrocarbon group, which may have a heteroatom that is O or N, and "A" is a hydrogen atom, a C3-C30 monovalent alicyclic group, which may have a heteroatom that is O or N, or a C6-C30 aryl group. "*" represents the bonding position.

The divalent chain hydrocarbon group represented by $L_1$ in Formula (4), which has a carbon number from 1 to 30, and may have a heteroatom that is O or N, may be in a form of normal chain or branched chain.

$L_1$ has more preferably a carbon number from 1 to 20, still more preferably from 1 to 10, and particularly preferably from 1 to 8.

When $L_1$ includes a heteroatom, the number of the heteroatom is preferably from 1 to 3, and more preferably 1 or 2.

$L_1$ may have a substituent. Preferable examples of the substituent of $L_1$ include a C1-C3 alkyl group, a hydroxy group, and a C1-C3 alkyl group in which 1 or 2 hydrogen atoms are substituted with hydroxy groups.

$L_1$ may include a urethane bond. When $L_1$ includes a urethane bond, the number of urethane bond may be 1 or 2.

Examples of $L_1$ may include the following structure.

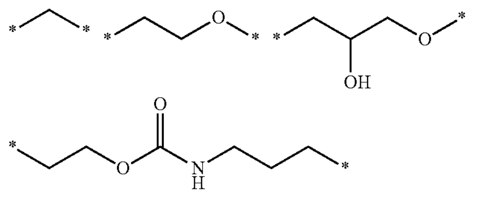

Examples of the C3-C20 monovalent alicyclic group, which may have a heteroatom that is O or N, and is represented by "A" in Formula (4), include a cyclopropyl group, a cyclobutyl group, a cyclopentyl group, a cyclohexyl group, a cyclohexenyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclooctadecyl group, a cycloicosyl group, a bicyclohexyl group, a norbornyl group, an isobornyl group, an adamantyl group, a morpholyl group, a piperidino group, a piperazino group, and a dioxane group. The carbon number of the monovalent alicyclic group is preferably from 5 to 12, and more preferably from 6 to 10.

Examples of the aromatic structure of the C6-C30 aryl group, represented by "A" in Formula (4) include a phenyl structure, a biphenyl structure, a naphthyl structure, and an anthryl structure "A" may have a substituent. Preferable examples of the substituent of "A" include a C1-C6 alkyl group such as a methyl group and an ethyl group; a hydroxy group; a C1-C6 alkyl group substituted with one or two hydroxy groups; an aryl group; a C3-C6 cycloalkyl group such as a cyclopentyl group and a cyclohexyl group; a tolyl group; a xylyl group; a cumyl group; a styryl group; and an alkoxyphenyl group such as a methoxyphenyl group, an ethoxyphenyl group, and a propoxyphenyl group.

Examples of "A" include the following. "*" represents the bonding position.

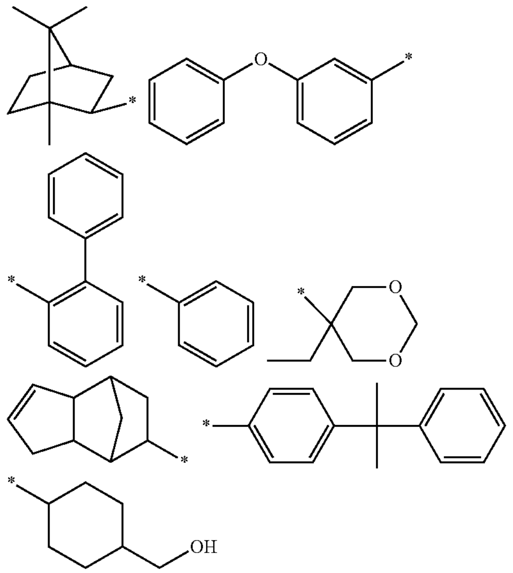

The total number of carbon atoms in the organic group represented by Formula (4) is preferably from 1 to 30, and more preferably from 1 to 20.

Each of $R^7$ and $R^8$ in Formula (3) is independently a monovalent organic group which may have a ring structure, or a hydrogen atom, and $R^7$ and $R^8$ may bond together to form a ring.

Preferable examples of $R^7$ and $R^8$ include a C1 to C30 monovalent hydrocarbon groups which may have a heteroatom that is O or N. The chain hydrocarbon group may be in a form of normal chain or branched chain, may be saturated or unsaturated, and may have a substituent.

The carbon number is more preferably from 1 to 20, and still more preferably from 1 to 10.

Examples of the organic group of $R^7$ and $R^8$ include a C1-C30 alkyl group such as a methyl group, an ethyl group, and a propyl group which may have a hetero atom that is O or N. It is preferable that either of $R^7$ and $R^8$ is a hydroxyethyl group or a butoxymethyl group, and the other is a hydrogen atom. Preferable examples of the monomer include the following monomer.

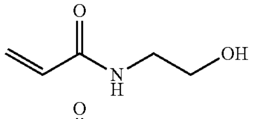

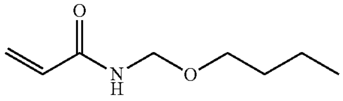

Examples of the acrylic monomer (B) where $R^7$ and $R^8$ bond together to form a ring include the following.

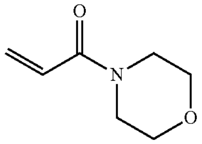

Although there is no particular restriction on the molecular weight of the acrylic monomer (B), the weight average molecular weight is preferably from 80 to 500, more preferably from 100 to 400, and particularly preferably from 130 to 320.

Examples of a compound suitable as the acrylic monomer (B) include the compounds used in Examples described later.

The content of the di-(meth)acrylic monomer (A) in the photo-curable composition of this disclosure is preferably from 300 parts by mass to 950 parts by mass with respect to 1000 parts by mass of the total content of (meth)acrylic monomer components contained in the photo-curable composition, and more preferably from 450 parts by mass to 900 parts by mass.

The "total content of (meth)acrylic monomer components" is the total of the contents of all monomers having a (meth)acryloyl group or a (meth)acryloyloxy group included in the photo-curable composition of this disclosure.

The total content of the di-(meth)acrylic monomer (A) and the acrylic monomer (B) in the photo-curable composition of this disclosure is preferably 800 parts by mass or more with respect to 1000 parts by mass of the total content of (meth)acrylic monomer components contained in the photo-curable composition, more preferably 900 parts by mass or more, and still more preferably 950 parts by mass or more.

<Photopolymerization Initiator>

The photo-curable composition of this disclosure includes a photopolymerization initiator.

There is no particular restriction on the photopolymerization initiator, insofar as it generates radicals when it is irradiated with light, however it is preferable that it generates radicals at the wavelength of light used in optical shaping.

The wavelength of light used in optical shaping is in general from 365 nm to 500 nm, but practically preferably from 365 nm to 430 nm, and more preferably from 365 nm to 420 nm.

Examples of the photopolymerization initiator which generates radicals at the wavelength of light used in optical shaping include an alkylphenone compound, an acylphosphine oxide compound, a titanocene compound, an oxime ester compound, a benzoin compound, an acetophenone compound, a benzophenone compound, a thioxanthone compound, an α-acyloxime ester compound, a phenylglyoxylate compound, a benzyl compound, an azo compound, a diphenyl sulfide compound, an organic dye compound, an iron phthalocyanine compound, a benzoin ether compound, and an anthraquinone compound.

Among these, an alkylphenone compound, and an acylphosphine oxide compound are preferable from the viewpoint of reactivity, etc.

Examples of an alkylphenone compound include 1-hydroxycyclohexyl phenyl ketone (OMNIRAD 184, produced by IGM Resins B. V.).

Examples of an acylphosphine oxide compound include bis(2,4,6-trimethylbenzoyl)phenylphosphine oxide (OMNIRAD 819, produced by IGM Resins B. V), and 2,4,6-trimethylbenzoyl diphenyl phosphine oxide (OMNIRAD TPO, produced by IGM Resins B. V.).

The photo-curable composition of this disclosure may include only one kind of photopolymerization initiator, or may include two or more kinds thereof.

The content of a photopolymerization initiator in the photo-curable composition of this disclosure (when there are two or more kinds, the total content) is preferably from 0.1% by mass to 10% by mass, more preferably from 0.2% by mass to 5% by mass, and particularly preferably from 0.3% by mass to 3% by mass.

(Other Components)

The photo-curable composition of this disclosure may include as needed one or more kinds of other components than the di-(meth)acrylic monomer (A), the acrylic monomer (B), and a photopolymerization initiator.

When the photo-curable composition includes such other components, the total mass of the di-(meth)acrylic monomer (A), the acrylic monomer (B), and the photopolymerization initiator is preferably 30% by mass or more with respect to the total amount of the photo-curable composition, more preferably 50% by mass or more, still more preferably 70% by mass or more, still more preferably 80% by mass or more, still more preferably 90% or more, and particularly preferably 95% by mass or more.

Other components may be, for example, monomers other than the di-(meth)acrylic monomer (A) and the acrylic monomer (B).

When a photo-curable composition includes a monomer other than the di-(meth)acrylic monomer (A) and the acrylic monomer (B) as another component, the content of the monomer as another component is preferably 50% or less with respect to the total mass of the di-(meth)acrylic monomer (A) and the acrylic monomer (B), more preferably 30% or less, still more preferably 20% or less, and particularly preferably 10% or less. There is no particular restriction on the lower limit of the content of the monomer as another component, and it may be 0%.

Examples of such other components include a coloring material, a monomer other than the di-(meth)acrylic monomer and the (meth)acrylic monomer, a coupling agent such as a silane coupling agent (for example, 3-acryloxypropyltrimethoxysilane), and a rubber agent, an ion trapping agent, an ion exchanger, a leveling agent, a plasticizer, an additive such as an defoaming agent, and a thermal polymerization initiator.

When a photo-curable composition of this disclosure includes a thermal polymerization initiator, combined execution of photo-curing and thermal curing becomes possible. Examples of a thermal polymerization initiator include a thermal radical generator and an amine compound.

There is no particular restriction on the method for preparing a photo-curable composition of this disclosure, and for example a di-(meth)acrylic monomer (A), an acrylic monomer (B), and a photopolymerization initiator (as well as other components as needed) are mixed together.

There is no particular restriction on the means of mixing the relevant components, and examples of such means include ultrasonic melting, a double arm agitator, a roll kneading machine, a twin-screw extruder, a ball mill kneading machine, and a planetary agitator.

A photo-curable composition of the present Embodiment may be prepared by mixing the components, then filtering the mixture through a filter to remove impurities, and further performing vacuum degassing.

[Photo-Cured Product]

There is no particular restriction on the method of photo-curing a photo-curable composition of this disclosure, and any publicly known method and device may be used. There is, for example, a method in which a step of forming a thin film composed of a photo-curable composition of this disclosure, and a step of forming a cured layer by irradiating the thin film with light are repeated multiple times to layer a plurality of cured layers one on another to complete a photo-cured product with a desired shape. In this regard, the obtained photo-cured product may be used as it is, or after improving its mechanical properties, shape stability, etc. by performing post curing by additional light irradiation, heating, etc.

There is no particular restriction on the glass transition temperature (Tg) after photo-curing of a photo-curable composition of this disclosure, however from the viewpoint of flexural strength and flexural modulus the glass transition temperature (Tg) after photo-curing is preferably 70° C. or higher, and more preferably 80° C. or higher.

Further, from the viewpoint of fracture toughness, the glass transition temperature (Tg) after photo-curing is preferably 140° C. or lower.

[Dental Product]

There is no particular restriction on a dental product including a cured product of a photo-curable composition of this disclosure (i.e., an optically shaped product), and it may be used in an artificial tooth, a prosthesis, a medical device used in the oral cavity, etc. Use in a medical device used in the oral cavity is preferable and use in a mouthpiece is particularly preferable. It is preferable to use a cured product of a photo-curable composition of this disclosure at least as part of a dental product. Examples of the medical device used in the oral cavity include a mouthpiece for orthodontics, a splint such as a splint for occlusal adjustment, and a splint for treating temporomandibular disorder, and a mouthpiece for treating sleep apnea syndrome.

When a cured product of a photo-curable composition of this disclosure is used, a medical device, which is excellent in feel of use in the oral cavity, and capable of exhibiting sufficient strength and hardness can be produced. Further, when it is fabricated to a medical device used in the oral cavity such as a splint, attachment and detachment can be easy and the durability in repeating the attachment and detachment can be improved.

EXAMPLES

The present invention will be specifically described below with reference to Examples, however the invention is not restricted by the Examples.

Examples 1 to 28, and Comparative Examples 1 to 12

<Preparation of Photo-Curable Composition>

The components listed in the following Tables 1-1 to 1-6 were mixed together to yield a photo-curable composition.

<Measurement and Evaluation>

Using the yielded photo-curable compositions, the following measurements and evaluations were performed. The results are shown in Tables 1-1 to 1-6.

(Viscosity of Photo-Curable Composition)

The viscosity of a photo-curable composition was measured with an E type viscometer under the conditions of 25° C. and 50 rpm.

(Flexural Strength and Flexural Modulus of Optically Shaped Product)

Using a 3D printer (CARA PRINT 4.0, Kulzer GmbH), the yielded photo-curable composition was shaped into a shaped product in a size of 64 mm×10 mm×thickness 3.3 mm. The obtained shaped product was irradiated with ultraviolet rays having a wavelength of 365 nm under the condition of 10 J/cm$^2$ to perform main curing, thereby yielding an optically shaped product.

The yielded optically shaped product (hereinafter referred to as "test piece") was stored in a thermostatic water bath at 37±1° C. for 50±2 hours.

Thereafter, the test piece was taken out from the thermostatic water bath, and the flexural strength and the flexural modulus of the taken-out test piece were respectively measured according to ISO 20795-1:2008. These measurements were carried out using a universal testing machine (manufactured by INTESCO Co., Ltd.) at a test speed of 5±1 mm/min.

(Total Work of Fracture by Fracture Toughness Test Based on Bending Test)

Using a 3D printer (CARA PRINT 4.0, Kulzer GmbH), the yielded photo-curable composition was shaped into a shaped product in a size of 39 mm×8 mm×thickness 4 mm. The obtained shaped product was irradiated with ultraviolet rays having a wavelength of 365 nm under the condition of 10 J/cm$^2$ to perform main curing of the shaped product, thereby yielding an optically shaped product.

The yielded optically shaped product (hereinafter referred to as "test piece") was notched according to ISO 20795-1:2008 and stored in a thermostatic water bath at 37±1° C. for 7 days±2 hours.

Thereafter, the test piece was taken out from the thermostatic water bath, and the taken-out test piece was subjected to a fracture toughness test based on a bending test according to ISO 20795-1:2008 to measure the total work of fracture (J/m$^2$). The fracture toughness test (that is, measurement of total work of fracture) by a bending test was carried out using a universal testing machine (manufactured by INTESCO Co., Ltd.) at a push-in speed of 1.0±0.2 mm/min.

(Evaluation of Attachment and Detachment)

Attachment and Detachment Test on Attachment and Detachment Test Piece

Using a 3D printer (CARA PRINT 4.0, Kulzer GmbH), the yielded photo-curable composition was shaped into a shaped product with the shape shown in FIG. 1A with a thickness of 2 mm. The obtained shaped product was irradiated with ultraviolet rays having a wavelength of 365 nm under the condition of 10 J/cm$^2$ to perform main curing of the shaped product, thereby yielding an optically shaped product.

Figure 1B:
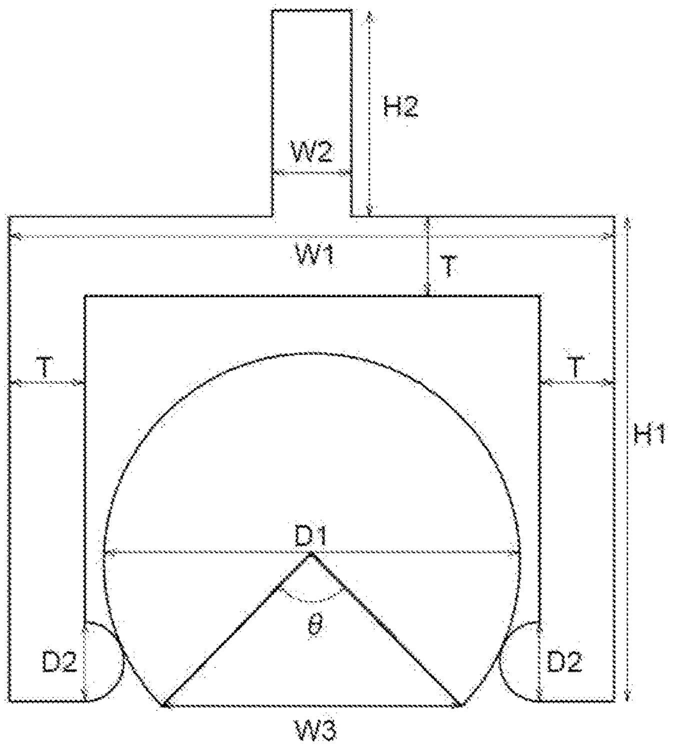
FIG. 1B is a schematic diagram showing the attachment and detachment test piece in a state attached to an object in the attachment and detachment test.

The yielded optically shaped product (hereinafter referred to as "test piece") was attached to an object for attachment and detachment as shown in FIG. 1B, and moved up and down at a travelling speed of 120.0±2.0 mm/min using a universal testing machine (manufactured by INTESCO Co., Ltd.) for evaluation of attachment and detachment. The object for attachment and detachment was prepared by cutting a SUS 304-made cylinder having a diameter of 10 mm such that the length of the chord became 7.07 mm in a circular cross section. During the test, the object was placed such that the cut surface was a bottom surface in contact with the ground. After 10,000 cycles of up-and-down movements, the test piece was visually examined. In a case where there was no change in the shape and no fracture after the test, it was rated as "A". In a case where there was some change in the shape but no fracture after the test, it was rated as "B". In a case where there was a fracture after the test, it was rated as "C".

In FIGS. 1A and 1B, T represents the thickness, D2 represents the diameter of the semicircle, H1 and H2 represent the height of each indicated portion, and W1 and W2 represent the width of each indicated portion. In FIG. 1B, D1 represents the diameter of the cross section of the cylinder before cutting the bottom surface of the object for attachment and detachment, 0 represents the apical angle of the triangle formed by connecting the center of the circle of the cross section of the cylinder with each edge of the bottom surface, and W3 represents the width of the bottom surface.

Where, T=2 mm, D1=10 mm, D2=2 mm, W1=15 mm, W2=2 mm, W3=7.07 mm, H1=12 mm, H2=5 mm, and 0=135°. Further, the length of the test piece shown in FIGS. 1A and 1B is 10 mm.

TABLE 1-1

| | | | Number of functional groups | Mw | Example 1 | Example 2 | Example 3 | Example 4 | Example 5 | Example 6 | Example 7 | Example 8 |
|---|---|---|---|---|---|---|---|---|---|---|---|---|
| Composition | (1) Urethane (meth)acrylic monomer | UDA | 2 | 442.51 | 700 | 800 | 900 | 700 | 800 | 700 | 600 | 700 |
| | | UDMA | 2 | 470.56 | | | | | | | | |
| | | AH600 | 2 | 612.67 | | | | | | | | |
| | | MMD-352 | 2 | 632.67 | | | | | | | | |
| | | KRM-076 | 2 | 448.47 | | | | | | | | |
| | | KRM-077 | 2 | 438.48 | | | | | | | | |
| | (2) (Meth)acrylic monomer | IB-XA | 1 | 208.30 | | | | | | | | |
| | | POB-A | 1 | 254.28 | | | | 300 | | 200 | 200 | |
| | | A-LEN-10 | 1 | 268.31 | | | | | | | 200 | |
| | | ACMO | 1 | 141.17 | 300 | | | | | | | |
| | | PO-A | 1 | 192.21 | | 200 | | | | | | 300 |
| | | 4EG | 2 | 330.37 | | | | | | | | |
| | | 4EG-A | 2 | 302.32 | | | | | | | | |
| | | PHOTO-MER4184 | 1 | 215.25 | | | 100 | | | | | |
| | | SR531 | 1 | 200.23 | | | | | 200 | | | |
| | | M-600A | 1 | 222.24 | | | | | | 100 | | |
| | | 2HPA | 1 | 130.14 | | | | | | | | |
| | | FA511AS | 1 | 204.26 | | | | | | | | |
| | | M-110 | 1 | 310.39 | | | | | | | | |
| | | CHDMMA | 1 | 198.26 | | | | | | | | |
| | (3) Photoinitiator | Omnirad 819 | | | 10 | 10 | 10 | 10 | 10 | 10 | 10 | 10 |
| | | Omnirad 184 | | | | | | | | | | |
| | | Omnirad TPO | | | | | | | | | | |
| Number of acryloyl groups (%) | | | | | 100.00 | 100.00 | 100.00 | 100.00 | 100.00 | 100.00 | 100.00 | 100.00 |
| Evaluation | (1) Viscosity (mPa · s) | | | | 646 | 748 | 2850 | 575 | 1270 | 782 | 539 | 309 |
| | (2) Flexural strength (MPa) | | | | 80 | 70 | 79 | 70 | 69 | 61 | 61 | 51 |
| | (3) Flexural modulus (MPa) | | | | 2344 | 2180 | 2239 | 2404 | 2110 | 2051 | 2230 | 1530 |
| | (4) Total work of fracture ($J/m^2$) | | | | 766 | 478 | 377 | 572 | 308 | 796 | 937 | 958 |
| | (5) Attachment and detachment rating | | | | A | A | A | A | A | A | A | A |

TABLE 1-2

| | | | Number of functional groups | Mw | Example 9 | Example 10 | Example 11 | Example 12 | Example 13 | Example 14 | Example 15 | Example 16 |
|---|---|---|---|---|---|---|---|---|---|---|---|---|
| Composition | (1) Urethane (meth)acrylic monomer | UDA | 2 | 442.51 | | | | | | | | |
| | | UDMA | 2 | 470.56 | 700 | 600 | 700 | 570 | 700 | 580 | 600 | |
| | | AH600 | 2 | 612.67 | | | | | | | | 760 |
| | | MMD-352 | 2 | 632.67 | | | | | | | | |
| | | KRM-076 | 2 | 448.47 | | | | | | | | |
| | | KRM-077 | 2 | 438.48 | | | | | | | | |

TABLE 1-2-continued

| | | | Number of functional groups | Mw | Example 9 | Example 10 | Example 11 | Example 12 | Example 13 | Example 14 | Example 15 | Example 16 |
|---|---|---|---|---|---|---|---|---|---|---|---|---|
| | (2) (Meth)acrylic monomer | I8-XA | 1 | 208.30 | | | | | | | | |
| | | POB-A | 1 | 254.28 | | 200 | 200 | 130 | 300 | 420 | 200 | 190 |
| | | A-LEN-10 | 1 | 268.31 | | | | | | | | |
| | | ACMO | 1 | 141.17 | | | | | | | | 50 |
| | | PO-A | 1 | 192.21 | | | | | | | | |
| | | 4EG | 2 | 330.37 | | | | | | | | |
| | | 4EG-A | 2 | 302.32 | | | | | | | | |
| | | PHOTO-MER4184 | 1 | 215.25 | | | | | | | | |
| | | SR 531 | 1 | 200.23 | | | | | | | | |
| | | M-600A | 1 | 222.24 | | | 100 | 300 | | | 200 | |
| | | 2HPA | 1 | 130.14 | 300 | 200 | | | | | | |
| | | FA511AS | 1 | 204.26 | | | | | | | | |
| | | M-110 | 1 | 310.39 | | | | | | | | |
| | | CHDMMA | 1 | 198.26 | | | | | | | | |
| | (3) Photoinitiator | Omnirad 819 | | | 10 | 10 | 10 | 10 | 10 | 10 | 10 | 10 |
| | | Omnirad 184 | | | | | | | | | | |
| | | Omnirad TPO | | | | | | | | | | |
| Number of acryloyl groups (%) | | | | | 43.65 | 47.87 | 29.36 | 43.45 | 28.39 | 40.12 | 39.81 | 100.00 |
| Evaluation | (1) Viscosity (mPa · S) | | | | 380 | 167 | 956 | 637 | 544 | 186 | 585 | 4730 |
| | (2) Flexural strength (MPa) | | | | 60 | 60 | 81 | 63 | 86 | 59 | 71 | 66 |
| | (3) Flexural modulus (MPa) | | | | 1741 | 1812 | 2409 | 1938 | 2475 | 2104 | 2103 | 2296 |
| | (4) Total work of fracture ($J/m^2$) | | | | 608 | 532 | 263 | 431 | 260 | 359 | 340 | 586 |
| | (5) Attachment and detachment rating | | | | A | A | A | A | A | A | A | A |

TABLE 1-3

| | | | Number of functional groups | Mw | Example 17 | Example 18 | Example 19 | Example 20 | Example 21 | Example 22 | Example 23 | Example 24 |
|---|---|---|---|---|---|---|---|---|---|---|---|---|
| Composition | (1) Urethane (meth)acrylic monomer | UDA | 2 | 442.51 | | | | | | | | |
| | | UDMA | 2 | 470.56 | | | | | | | | |
| | | AH600 | 2 | 612.67 | 580 | 500 | | | | | | |
| | | MMD-352 | 2 | 632.67 | | | 520 | 700 | 656 | 550 | 500 | |
| | | KRM-076 | 2 | 448.47 | | | | | | | | 450 |
| | | KRM-077 | 2 | 438.43 | | | | | | | | |
| | (2) (Meth)acrylic monomer | IB-XA | 1 | 208.30 | | | | | | 100 | | |
| | | POB-A | 1 | 254.28 | 270 | 300 | 300 | 200 | 164 | 350 | 400 | 550 |
| | | A-LEN-10 | 1 | 268.31 | | | | | | | | |
| | | ACMO | 1 | 141.17 | | | | | | | 100 | |
| | | PO-A | 1 | 192.21 | | | | | | | | |
| | | 4EG | 2 | 330.37 | 150 | | | | | | | |
| | | 4EG-A | 2 | 302.32 | | | 180 | | | | | |
| | | PHOTO-MER4184 | 1 | 215.25 | | | | 100 | | | | |
| | | SR531 | 1 | 200.23 | | | | | | | | |
| | | M-600A | 1 | 222.24 | | | | | | | | |
| | | 2HPA | 1 | 130.14 | | | | | | | | |
| | | FA511AS | 1 | 204.26 | | 200 | | | | | | |
| | | M-110 | 1 | 310.39 | | | | | | | | |
| | | CHDMMA | 1 | 198.26 | | | | | 180 | | | |
| | (3) Photoinitiator | Omnirad 819 | | | 10 | 10 | 10 | 10 | 10 | 10 | 10 | 10 |
| | | Omnirad 184 | | | | | | | | | | |
| | | Omnirad TPO | | | | | | | | | | |
| Number of acryloyl groups (%) | | | | | 76.49 | 100.00 | 100.00 | 100.00 | 100.00 | 100.00 | 100.00 | 100.00 |
| Evaluation | (1) Viscosity (mPa · s) | | | | 569 | 404 | 516 | 5860 | 3990 | 872 | 699 | 339 |
| | (2) Flexural strength (MPa) | | | | 50 | 55 | 58 | 61 | 68 | 50 | 62 | 52 |

TABLE 1-3-continued

| | Number of functional groups | Mw | Example 17 | Example 18 | Example 19 | Example 20 | Example 21 | Example 22 | Example 23 | Example 24 |
|---|---|---|---|---|---|---|---|---|---|---|
| (3) Flexural modulus (MPa) | | | 1992 | 2292 | 2158 | 2277 | 2462 | 2335 | 2407 | 2334 |
| (4) Total work of fracture (J/m$^2$) | | | 479 | 635 | 431 | 624 | 652 | 779 | 945 | 888 |
| (5) Attachment and detachment rating | | | A | A | A | A | A | A | A | A |

TABLE 1-4

| | | | Number of functional groups | Mw | Example 25 | Example 26 | Example 27 | Example 28 |
|---|---|---|---|---|---|---|---|---|
| Composition | (1) Urethane (meth)acrylic monomer | UDA | 2 | 442.51 | | | | 600 |
| | | UDMA | 2 | 470.56 | 570 | | | |
| | | AH600 | 2 | 612.67 | | | | |
| | | MMD-352 | 2 | 632.67 | | | | |
| | | KRM-076 | 2 | 448.47 | | 450 | | |
| | | KRM-077 | 2 | 438.46 | | | 450 | |
| | (2) (Meth)acrylic monomer | IB-XA | 1 | 208.30 | 138 | | | 200 |
| | | POB-A | 1 | 254.28 | | 556 | 550 | |
| | | A-LEN-10 | 1 | 268.31 | | | | |
| | | ACMO | 1 | 141.17 | | | | |
| | | PO-A | 1 | 192.21 | | | | |
| | | 4EG | 2 | 330.37 | | | | |
| | | 4EG-A | 2 | 302.32 | | | | |
| | | PHOTOMER4184 | 1 | 215.25 | | | | |
| | | SR531 | 1 | 200.23 | | | | |
| | | M-600A | 1 | 222.24 | 300 | | | |
| | | 2HPA | 1 | 130.14 | | | | |
| | | FA511AS | 1 | 204.26 | | | | |
| | | M-110 | 1 | 310.39 | | | | 200 |
| | | CHDMMA | 1 | 198.26 | | | | |
| | (3) Photoinitiator | Omnirad 819 | | | | | | 10 |
| | | Omnirad 184 | | | 10 | 10 | 10 | |
| | | Omnirad TPO | | | 10 | | 10 | |
| Number of acryloyl groups (%) | | | | | 43.45 | 100.00 | 100.00 | 100.00 |
| Evaluation | (1) Viscosity (mPa · s) | | | | 665 | 331 | 259 | 524 |
| | (2) Flexural strength (MPa) | | | | 61 | 51 | 65 | 60 |
| | (3) Flexural modulus (MPa) | | | | 1922 | 2311 | 2487 | 2040 |
| | (4) Total work of fracture (J/m$^2$) | | | | 441 | 893 | 743 | 889 |
| | (5) Attachment and detachment rating | | | | A | A | A | A |

TABLE 1-5

| | | | Number of functional groups | Mw | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|---|---|
| Composition | (1) Urethane (meth)acrylic monomer | UDA | 2 | 442.51 | | | | | | | | |
| | | UDMA | 2 | 470.56 | 700 | | | | | | | |
| | | AH600 | 2 | 612.67 | | | | | | | | |
| | | MMD-352 | 2 | 632.67 | | | | | | | | |
| | | KRM-076 | 2 | 448.47 | | | | | | | | |
| | | KRM-077 | 2 | 438.48 | | | | | | | | |
| | | EBECRYL | 3 | 1100.00 | | 700 | | | | | | |

TABLE 1-5-continued

| | | Number of functional groups | Mw | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|---|
| | 4100 | | | | | | | | | | |
| | EBECRYL 4740 | 3 | 1250.00 | | | 700 | | | | | |
| | UA-306T | 6 | 770.14 | | | | 600 | 630 | 630 | | |
| | UA-306H | 6 | 764.78 | | | | | | | 650 | 650 |
| (2) (Meth)acrylic monomer | IB-XA | 1 | 208.30 | | | | | | | | |
| | POB-A | 1 | 254.28 | | 300 | 300 | | | 200 | | 200 |
| | A-LEN-10 | 1 | 268.31 | | | | | | | | |
| | ACMO | 1 | 141.17 | | | | | | | | |
| | PO-A | 1 | 192.21 | | | | 400 | | | | |
| | 4EG | 2 | 330.37 | | | | | | | | |
| | 4EG-A | 2 | 302.32 | | | | | 370 | 170 | 350 | 150 |
| | PHOTO-MER4184 | 1 | 215.25 | | | | | | | | |
| | SR531 | 1 | 200.23 | | | | | | | | |
| | M-600A | 1 | 222.24 | | | | | | | | |
| | 2HPA | 1 | 130.14 | | | | | | | | |
| | FA511AS | 1 | 204.26 | | | | | | | | |
| | M-110 | 1 | 310.39 | | | | | | | | |
| | CHDMMA | 1 | 198.26 | | | | | | | | |
| | HEMA | 1 | 130.14 | | | | | | | | |
| | PO | 1 | 200.24 | | | | | | | | |
| (4) Acrylic monomer | ABE-300 | 2 | 468.60 | | | | | | | | |
| (3) Photoinitiator | Ir819 | | | 10 | 10 | 10 | 10 | 10 | 10 | 10 | 10 |
| | Ir184 | | | | | | | | | | |
| | TPO | | | | | | | | | | |
| Number of acryloyl groups (%) | | | | 0.00 | 100.00 | 100.00 | 100.00 | 100.00 | 100.00 | 100.00 | 100.00 |
| Evaluation | (1) Viscosity (mPa · s) | | | 192 | 1140 | 1200 | 260 | 407 | 560 | 409 | 548 |
| | (2) Flexural strength (MPa) | | | 87 | 3 | 3 | 85 | 80 | 77 | 53 | 71 |
| | (3) Flexural modulus (MPa) | | | 2460 | 37 | 30 | 3687 | 3811 | 3253 | 2801 | 3430 |
| | (4) Total work of fracture ($J/m^2$) | | | 123 | 22 | 160 | 13 | 22 | 17 | 25 | 16 |
| | (5) Attachment and detachment rating | | | C | A | A | C | C | C | C | C |

TABLE 1-6

| | | | Number of functional groups | Mw | Comparative Example 9 | Comparative Example 10 | Comparative Example 11 | Comparative Example 12 |
|---|---|---|---|---|---|---|---|---|
| Composition | (1) Urethane (meth)acrylic monomer | UDA | 2 | 442.51 | | | | |
| | | UDMA | 2 | 470.56 | | 550 | | |
| | | AH600 | 2 | 612.67 | | | | |
| | | MMD-352 | 2 | 632.67 | | | | |
| | | KRM-076 | 2 | 448.47 | | | | |
| | | KRM-077 | 2 | 433.48 | | | | |
| | | EBECRYL 4100 | 3 | 1100.00 | | | | |
| | | EBECRYL 4740 | 3 | 1250.00 | | | | |
| | | UA-300T | 6 | 770.74 | 450 | | | |
| | | UA-306H | 6 | 764.78 | | | | |
| | (2) (Meth)acrylic monomer | IB-XA | 1 | 208.30 | | | | |
| | | POB-A | 1 | 254.28 | 550 | | | |
| | | A-LEN-10 | 1 | 268.31 | | | 400 | 700 |
| | | ACMO | 1 | 141.17 | | | | |
| | | PO-A | 1 | 192.21 | | | | |

TABLE 1-6-continued

| | | Number of functional groups | Mw | Comparative Example 9 | Comparative Example 10 | Comparative Example 11 | Comparative Example 12 |
|---|---|---|---|---|---|---|---|
| | 4EG | 2 | 330.37 | | | | |
| | 4EG-A | 2 | 302.32 | | | | |
| | PHOTO-MER4184 | 1 | 215.25 | | | | |
| | SR531 | 1 | 200.23 | | | | |
| | M-600A | 1 | 222.24 | | | | |
| | 2HPA | 1 | 130.14 | | | | |
| | FA511AS | 1 | 204.26 | | | | |
| | M-110 | 1 | 310.39 | | | | |
| | CHDMMA | 1 | 198.26 | | | | |
| | HEMA | 1 | 130.14 | | | | |
| | PO | 1 | 206.24 | | 450 | | |
| (4) Acrylic monomer | ABE-300 | 2 | 468.50 | | | 600 | 300 |
| (3) Photoinitiator | Ir819 | | | 10 | 10 | | |
| | Ir184 | | | | | | |
| | TPO | | | | | | |
| Number of acryloyl groups (%) | | | | 100.00 | 0.00 | 0.00 | 0.00 |
| Evaluation (1) Viscosity (mPa · s) | | | | 310 | 112 | 190 | 280 |
| (2) Flexural strength (MPa) | | | | 94 | 80 | 71 | 69 |
| (3) Flexural modulus (MPa) | | | | 2998 | 2361 | 2580 | 2728 |
| (4) Total work of fracture ($J/m^2$) | | | | 16 | 40 | 224 | 255 |
| (5) Attachment and detachment rating | | | | C | C | C | C |

In Tables 1-1 to 1-6, the numbers in the rows of "Composition" for each Example and each Comparative Example are expressed in parts by mass.

In Tables 1-1 to 1-6, each number in the row of "Number of acryloyl groups (%)" for each Example or each Comparative Example shows the percentage (%) of the number of acryloyl groups with respect to the total number of acryloyl groups and methacryloyl groups in a photo-curable composition.

<Di-(Meth)Acrylic Monomer (A) Having Two (Meth)Acryloyloxy Groups and Two Urethane Bonds>

The structures of the respective di-(meth)acrylic monomers (A) having two (meth)acryloyloxy groups and two urethane bonds described in Tables 1-1 to 1-6 are as follows.

UDA

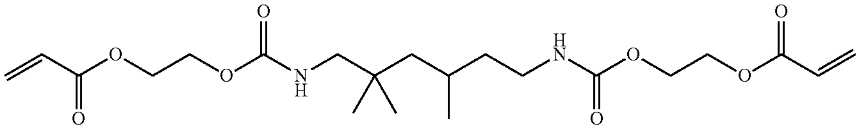

UDMA

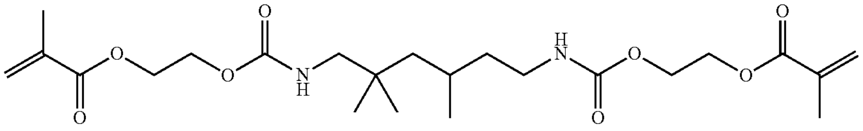

AH-600

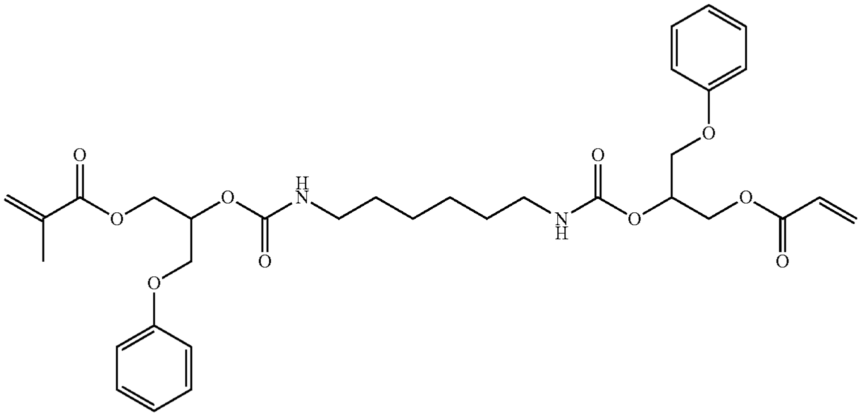

-continued

MMD-352

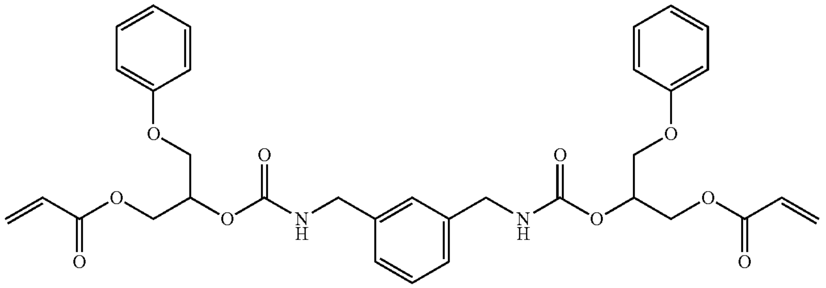

KRM-076

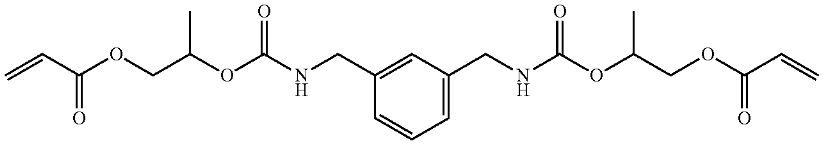

KRM-077

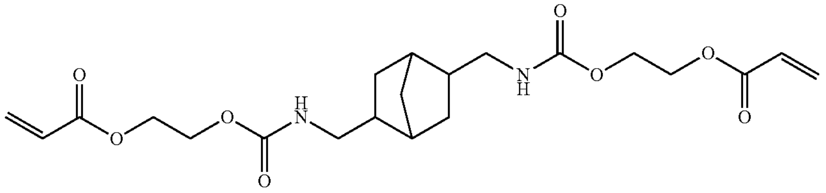

AH-600 is a urethane acrylic monomer produced by Kyoeisha Chemical Co., Ltd.

UDA, UDMA, MMD-352, KRM-076, and KRM-077 were produced as described below.

The explanations of the abbreviations in the following Production Examples are shown as follows.

HEA: Hydroxyethyl acrylate

TMHDI: 2,4,4-Trimethylhexane diisocyanate

DBTDL: Dibutyltin dilaurate

MEHQ: 4-Methoxyphenol

XDI: m-Xylylene diisocyanate

NBDI: Norbornene diisocyanate

Production Example 1: Production of UDA

Into a completely dried 1 liter 4-neck flask equipped with a stirring blade and a thermometer, 372 g (3.20 mol) of HEA and 0.71 g of DBTDL (0.1% by weight with respect to the total weight of HEA and TMHDI), and 0.35 g of MEHQ (0.05% by weight with respect to the total weight of HEA and TMHDI) were charged, and mixed with stirring to a uniform mixture, and then the temperature was raised to 60° C. Subsequently, 337 g (1.60 mol) of TMHDI was dropped over 1 hour. Since the internal temperature increased due to the heat of reaction during the dropping, the dropping amount was controlled so as to limit the temperature at 80° C. or lower. After dropping the whole amount, the reaction was carried out for 10 hours maintaining the temperature at 80° C., during which the progression of the reaction was traced by HPLC analysis to detect the end point of the reaction. By discharging the product from the reactor, 680 g of urethane acrylate (UDA) was obtained. The viscosity at 25° C. was 7100 mPa·s.

Production Example 2: Production of UDMA

Into a completely dried 1 liter 4-neck flask equipped with a stirring blade and a thermometer, 416 g (3.20 mol) of HEMA (the structure will be described later), 0.75 g of DBTDL (0.1% by weight with respect to the total weight of HEMA and TMHDI), and 0.38 g of MEHQ (0.05% by weight with respect to the total weight of HEMA and TMHDI) were charged, and mixed with stirring to a uniform mixture, and then the temperature was raised to 60° C. Subsequently, 337 g (1.60 mol) of TMHDI was dropped over 1 hour. Since the internal temperature increased due to the heat of reaction during the dropping, the dropping amount was controlled so as to limit the temperature at 80° C. or lower. After dropping the whole amount, the reaction was carried out for 10 hours maintaining the temperature at 80° C., during which the progression of the reaction was traced by HPLC analysis to detect the end point of the reaction. By discharging the product from the reactor, 720 g of urethane methacrylate (UDMA) was obtained. The viscosity at 25° C. was 8200 mPa·s.

Production Example 3: Production of MMD-352

Into a completely dried 1 liter 4-neck flask equipped with a stirring blade and a thermometer, 444 g (2.00 mol) of M-600A, 0.63 g of DBTDL (0.1% by weight with respect to the total weight of M-600A and XDI described later), and 0.32 g of MEHQ (0.05% by weight with respect to the total weight of M-600A and XDI) were charged, and mixed with stirring to a uniform mixture, and then the temperature was raised to 60° C. Subsequently, 188 g (1.00 mol) of XDI was dropped over 1 hour. Since the internal temperature increased due to the heat of reaction during the dropping, the dropping amount was controlled so as to limit the temperature at 80° C. or lower. After dropping the whole amount, the reaction was carried out for 10 hours maintaining the temperature at 80° C., during which the progression of the reaction was traced by HPLC analysis to detect the end point of the reaction. By discharging the product from the reactor, 600 g of urethane acrylate (MMD-352) was obtained. The viscosity at 65° C. was 6210 mPa·s.

Production Example 4: Production of KRM-076

Into a completely dried 1 liter 4-neck flask equipped with a stirring blade and a thermometer, 418 g (3.21 mol) of 2HPA (the structure will be described later), 0.72 g of DBTDL (0.1% by weight with respect to the total weight of 2HPA and XDI), and 0.36 g of MEHQ (0.05% by weight with respect to the total weight of 2HPA and XDI) were charged, and mixed with stirring to a uniform mixture, and then the temperature was raised to 60° C. Subsequently, 303 g (1.61 mol) of XDI was dropped over 1 hour. Since the internal temperature increased due to the heat of reaction during the dropping, the dropping amount was controlled so as to limit the temperature at 80° C. or lower. After dropping the whole amount, the reaction was carried out for 10 hours maintaining the temperature at 80° C., during which the progression of the reaction was traced by HPLC analysis to detect the end point of the reaction. By discharging the product from the reactor, 690 g of urethane acrylate (KRM-076) was obtained. The viscosity at 65° C. was 570 mPa·s.

Production Example 5: Production of KRM-077

Into a completely dried 1 liter 4-neck flask equipped with a stirring blade and a thermometer, 372 g (3.20 mol) of HEA, 0.70 g of DBTDL (0.1% by weight with respect to the total weight of HEA and NBDI), and 0.35 g of MEHQ (0.05% by weight with respect to the total weight of HEA and NBDI) were charged, and mixed with stirring to a uniform mixture, and then the temperature was raised to 60° C. Subsequently, 330 g (1.60 mol) of NBDI was dropped over 1 hour. Since the internal temperature increased due to the heat of reaction during the dropping, the dropping amount was controlled so as to limit the temperature at 80° C. or lower. After dropping the whole amount, the reaction was carried out for 10 hours maintaining the temperature at 80° C., during which the progression of the reaction was traced by HPLC analysis to detect the end point of the reaction. By discharging the product from the reactor, 670 g of urethane acrylate (KRM-077) was obtained. The viscosity at 65° C. was 930 mPa·s.

<(Meth)Acrylic Monomer not Pertinent to Di-(Meth) Acrylic Monomer (A) Having Two (Meth)Acryloyloxy Groups and Two Urethane Bonds>

In Tables 1-1 to 1-6, EBECRYL 4100 and EBECRYL 4740 are urethane acrylates produced by Daicel-Allnex Ltd. The details of the structure have not been disclosed by Daicel-Allnex Ltd. except that they are trifunctional and have functional groups shown in Table 2. UA-306T and UA-306H are produced by Kyoeisha Chemical Co., Ltd. The structures of UA-306T and UA-306H are shown below.

UA-306T

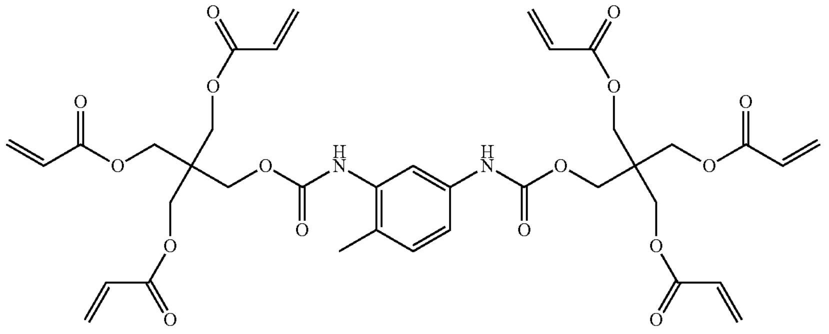

UA-306H

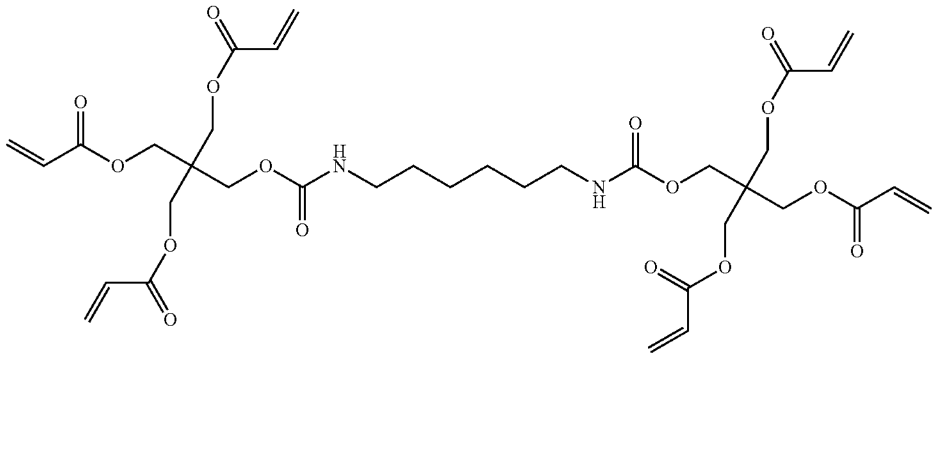

The numbers of methacryloyloxy groups, acryloyloxy groups, and acryloyl groups in one molecule of the di-(meth)acrylic monomer (A) or a (meth)acrylic monomer not pertinent to the di-(meth)acrylic monomer (A) are shown in Table 2.

TABLE 2

| | | Number of acryloyloxy groups | Number of methacryloyloxy groups | Number of urethane bonds |
|---|---|---|---|---|
| Di-(meth)acrylic monomer (A) having two (meth)acryloyloxy groups and two urethane bonds | UDA | 2 | 0 | 2 |
| | UDMA | 0 | 2 | 2 |
| | AH600 | 2 | 0 | 2 |
| | MMD-352 | 2 | 0 | 2 |
| | KRM-076 | 2 | 0 | 2 |
| | KRM-077 | 2 | 0 | 2 |
| Acrylic monomer not pertinent to di-(meth)acrylic monomer (A) | EBECRYL 4100 | 3 | 0 | at least 1 |
| | EBECRYL 4740 | 3 | 0 | at least 1 |
| | UA-306T | 6 | 0 | 2 |
| | UA-306H | 6 | 0 | 2 |

<Acrylic Monomer (B) Having One Acryloyl Group>

The structures of the acrylic monomers (B) having one acryloyl group shown in Tables 1-1 to 1-6 are respectively as follows.

IB-XA

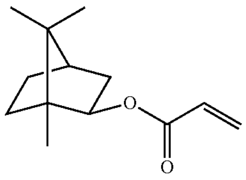

POB-A

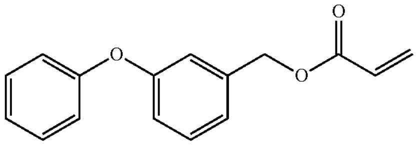

A-LEN-10

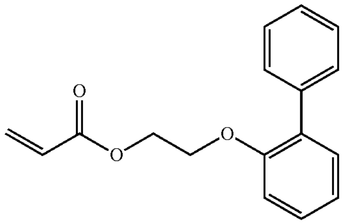

ACMO

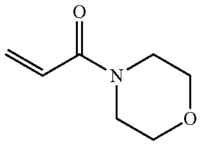

PO-A

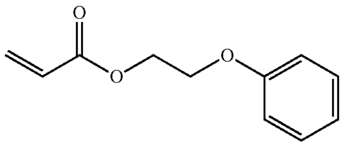

-continued

Photomer4184

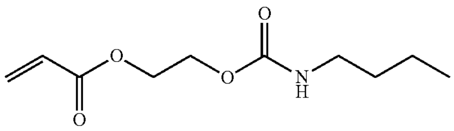

SR531

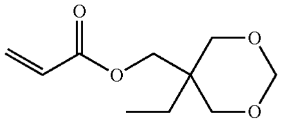

M-600A

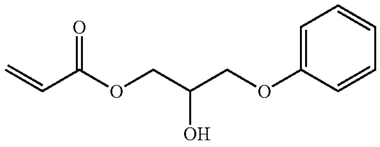

2HPA (HOP-A)

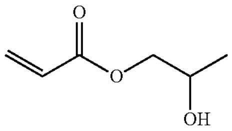

FA511AS

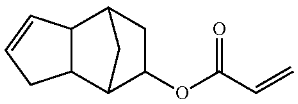

M-110

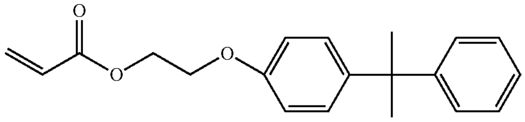

CHDMMA

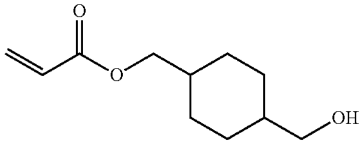

IB-XA, POB-A, PO-A, M-600A, and HOP-A are produced by Kyoeisha Chemical Co., Ltd. A-LEN-10 is produced by Shin-Nakamura Chemical Co., Ltd. ACMO is produced by KJ Chemicals Corporation. PHOTOMER 4184 is produced by IGM Resins. SR531 is produced by Arkema. FA511AS is produced by Hitachi Chemical Co., Ltd. M-110 is produced by Toagosei Co., Ltd. CHDMMA is produced by Nippon Kasei Chemical Co., Ltd.

<Monomer Not Pertinent to Acrylic Monomer (B) Having One Acryloyl Group and Aforedescribed Di-(Meth)Acrylic Monomer (A)>

In Tables 1-1 to 1-6, 4EG, 4EG-A, HEMA, and PO are produced by Kyoeisha Chemical Co., Ltd. ABE-300 is produced by Shin-Nakamura Chemical Co., Ltd. The respective structures are as follows.

Omnirad819

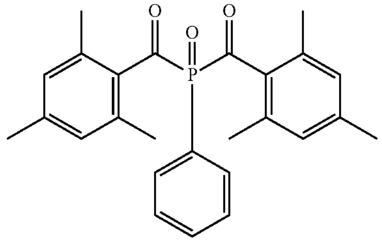

4EG

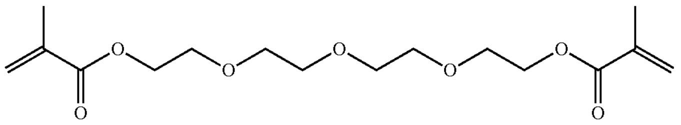

4EG-A

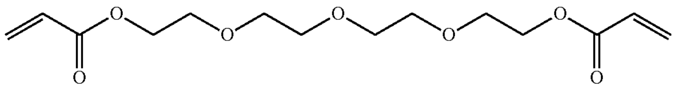

HEMA

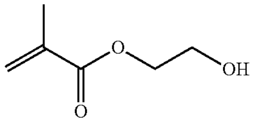

PO

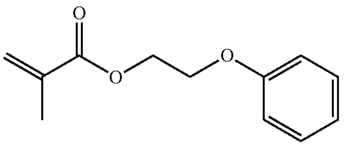

ABE-300

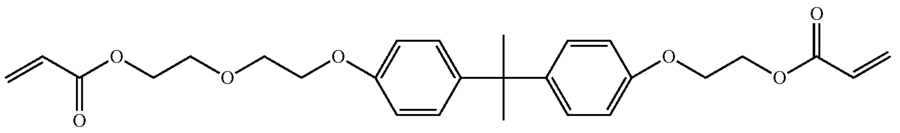

The numbers of acryloyl groups in one molecule of the acrylic monomer (B) having one acryloyl group, as well as the acrylic monomer not pertinent to the acrylic monomer (B) and the di-(meth)acrylic monomer (A) are shown in Table 3.

TABLE 3

| | | Number of acryloyl groups |
|---|---|---|
| Acrylic monomer (B) haying one acryloyl group | IB-XA | 1 |
| | POB-A | 1 |
| | A-LEN-10 | 1 |
| | ACMO | 1 |
| | PO-A | 1 |
| | Photomer 4184 | 1 |
| | SR531 | 1 |
| | M-600A | 1 |
| | 2HPA | 1 |
| | FA511AS | 1 |
| | M-110 | 1 |
| | CHDMMA | 1 |
| Acrylic monomer pertinent neither d to di-(meth)acrylic monomer (A) nor to acrylic monomer (B) | 4EG | 0 |
| | 4EG-A | 2 |
| | HEMA | 0 |
| | PO | 0 |

<Photopolymerization Initiator>

The respective structures of the photopolymerization initiators shown in Tables 1-1 to 1-6 are as follows.

-continued

Omnirad184

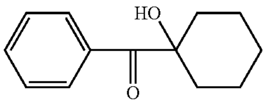

OmniradTPO

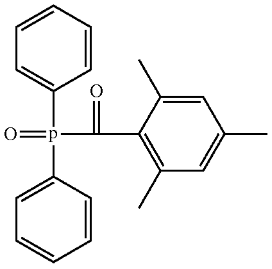

OMNIRAD 819 (acylphosphine oxide compound), OMNIRAD 184 (alkylphenone compound), and OMNIRAD TPO (acylphosphine oxide compound) are produced by IGM Resins.

As shown in Tables 1-1 to 1-6, a photo-curable composition of Examples including a di-(meth)acrylic monomer (A) having two (meth)acryloyloxy groups and two urethane bonds, and an acrylic monomer (B) having one acryloyl group, was superior in all of flexural strength, flexural modulus, and total work of fracture to the photo-curable compositions of Comparative Examples not including the aforedescribed monomers.

For example, it has become clear that a photo-curable composition of Example including the acrylic monomer (B) having one acryloyl group is superior in total work of fracture compared to a photo-curable composition including a monomer having one meta-acryloyl group (e.g., Comparative Examples 1 and 10).

Further, when Example 5 in which UDA was used as the di-(meth)acrylic monomer (A) was compared with Example 13 in which UDMA was used, Example 5 was superior in terms of total work of fracture. From this it has become clear that when an acrylate is used rather than a methacrylate as the di-(meth)acrylic monomer (A), better toughness can be obtained.

Further, in Examples in which ACMO or HPA was included as the acrylic monomer (B) (e.g., Example 1, and Example 9), the total work of fracture tended to be high. However, although not shown in the table, in these Examples the water absorption tended to increase due to the high content of ACMO, HPA, or the like. In contrast, in Examples using a monofunctional acrylic monomer having a ring structure such as POB-A as the acrylic monomer (B) (e.g., Examples 4 and 7), or in Examples using the same with another monomer (e.g., Example 10), it was possible to obtain reasonable flexural strength, flexural modulus, and total work of fracture while suppressing the water absorption.

In Examples including AH600 or MMD-352 as the di-(meth)acrylic monomer (A) (e.g., Example 16), the total work of fracture tended to be higher, but on the other hand the viscosity also tended to increase. In contrast, in Examples (Examples 24, 26, and 27), in which a monomer having a ring structure in the center, and having an alkylene structure, such as KRM-076 or KRM-077 was used as the di-(meth)acrylic monomer (A), a high total work of fracture could be attained, while suppressing the viscosity, and securing reasonable flexural strength and flexural modulus.

When used as a medical device to be used in the oral cavity such as a splint, a certain level of hardness and toughness are required, on the other hand, when the flexural strength is too high, the patient will be more likely to feel pain. Regarding this point of view, since in some Examples an excellent total work of fracture of 250 J/$m^2$ or higher (in some Examples even 500 J/$m^2$ or higher) could be obtained, while keeping the flexural strength within a range of 50 to 70 MPa, which demonstrated that such cured product was suitable for a medical device to be used in the oral cavity.

When used as a medical device to be used in the oral cavity such as a splint, the device is repeatedly attached and detached in the oral cavity. Therefore, the ease of attachment and detachment, and a high durability in repeating attachment and detachment are required.

In Examples, favorable evaluation results were obtained from the attachment and detachment test. Also in Comparative Examples 2 and 3 favorable evaluation results on the attachment and detachment test were obtained, however the flexural strength was less than 50 MPa, and the flexural modulus was less than 1500 MPa, which did not meet the specifications according to ISO 20795-2, and would be inadequate as the strength required for a medical device to be used in the oral cavity.

The entire disclosure of Japanese Patent Application 2019-068556 filed on 29 Mar. 2019 is incorporated herein by reference. All the literature, patent application, and technical standards cited herein are also herein incorporated to the same extent as provided for specifically and severally with respect to an individual literature, patent application, and technical standard to the effect that the same should be so incorporated by reference. The foregoing description of the exemplary embodiment of the invention has been presented for purposes of illustration and explanation, and it is not intended to be exhaustive or to limit the invention to the precise form disclosed. Obviously, possibility of many modifications or variations is obvious to those skilled in the art. The embodiments described above are selected and described in order to best explain the principles and practical applications of the invention, and to facilitate those skilled in the art to understand the invention as well as various embodiments or various modifications suitable for a particular intended use. The scope of the invention is intended to be defined by the following claims and their equivalents.

The invention claimed is:

1. A photo-curable composition comprising:

a di-acrylic monomer (A) having two acryloyloxy groups and two urethane bonds, an acrylic monomer (B) having one acryloyl group, and a photopolymerization initiator, wherein the di-acrylic monomer (A) is a compound represented by the following Formula (1):

(1)

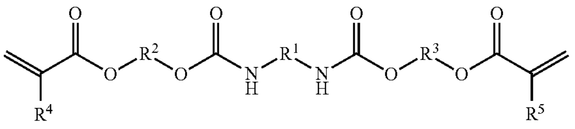

wherein, in Formula (1), $R^1$ is a divalent hydrocarbon group having an aromatic structure, or a divalent hydrocarbon group having an alicyclic structure, each of $R^2$ and $R^3$ is independently a divalent chain hydrocarbon group which may have a substituent, and each of $R^4$ and $R^5$ is a hydrogen atom, and a number of acryloyl groups accounts for 40% or more of a total of acryloyl groups and methacryloyl groups present in the photo-curable composition.

2. The photo-curable composition according to claim 1, wherein a ratio of a number of acryloyl groups with respect to a total number of acryloyl groups and methacryloyl groups in the photo-curable composition is 100% or more.

3. The photo-curable composition according to claim 1, wherein a cured product obtained by curing the photo-curable composition exhibits a flexural strength of from 50 to 70 MPa, a flexural modulus of from 1,500 to 2,000 MPa, and a total work of fracture of 250 J/$m^2$ or more.

4. The photo-curable composition according to claim 1, wherein, in Formula (1), $R^1$ is a C6-C12 divalent hydrocarbon group having an aromatic structure, or a C6-C12 divalent hydrocarbon group having an alicyclic structure, and each of $R^2$ and $R^3$ is independently a C6-C12 divalent chain hydrocarbon group having no substituent.

5. The photo-curable composition according to claim 1, wherein the acrylic monomer (B) comprises at least one of a compound represented by the following Formula (2) or a compound represented by the following Formula (3):

(2)

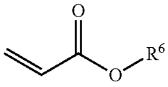

-continued (3)

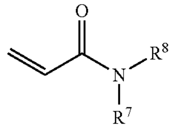

wherein, in Formula (2), $R^6$ is a monovalent organic group which may have a ring structure, and wherein, in Formula (3), each of $R^7$ and $R^8$ is independently a monovalent organic group which may have a ring structure, or a hydrogen atom, and $R^7$ and $R^8$ may together form a ring.

6. The photo-curable composition according to claim 5, wherein the acrylic monomer (B) comprises a compound represented by Formula (2), and $R^6$ in Formula (2) is a C6-C20 monovalent organic group having a ring structure.

7. The photo-curable composition according to claim 1, wherein a weight average molecular weight of the di-acrylic monomer (A) is from 380 to 700.

8. The photo-curable composition according to claim 1, wherein a weight average molecular weight of the acrylic monomer (B) is from 130 to 320.

9. The photo-curable composition according to claim 1, wherein a content of the di-acrylic monomer (A) is from 300 parts by mass to 950 parts by mass with respect to 1,000 parts by mass of a total content of (meth)acrylic monomer components contained in the photo-curable composition.

10. The photo-curable composition according to claim 1, wherein a total content of the di-acrylic monomer (A) and the acrylic monomer (B) is 800 parts by mass or more with respect to 1,000 parts by mass of a total content of (meth) acrylic monomer components contained in the photo-curable composition.

11. A photo-curable composition comprising a photopolymerizable component and a photopolymerization initiator, wherein a cured product obtained by curing the photo-curable composition exhibits a flexural modulus from 1,500 MPa to 2,500 MPa, and a total work of fracture of 250 J/$m^2$ or more, wherein the photopolymerizable component comprises a di-acrylic monomer (A) having two (meth)acryloyloxy groups and two urethane bonds, and wherein the di-acrylic monomer (A) is a compound represented by the following Formula (1):

(1)

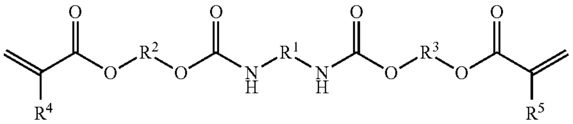

wherein, in Formula (1), $R^1$ is a divalent hydrocarbon group having an aromatic structure, or a divalent hydrocarbon group having an alicyclic structure, each of $R^2$ and $R^3$ is independently a divalent chain hydrocarbon group which may have a substituent, each of $R^4$ and $R^5$ is a hydrogen atom, and a number of acryloyl groups accounts for 40% or more of a total of acryloyl groups and methacryloyl groups present in the photo-curable composition.

12. The photo-curable composition according to claim 1, wherein a viscosity measured using an E type viscometer at 25° C. and 50 rpm is from 20 mPa·s to 3,000 mPa·s.

13. The photo-curable composition according to claim 1, wherein the photo-curable composition is for optical shaping.

14. A cured product of the photo-curable composition according to claim 1.

15. A dental product comprising the cured product of the photo-curable composition according to claim 14.

16. The dental product according to claim 15, wherein the dental product is a medical device which is used in an oral cavity.

* * * * *